United States Patent [19]

Van Peppen

[11] 4,422,954
[45] Dec. 27, 1983

[54] METHOD TO RESTORE THE METAL CONTENT OF A NOBLE METAL HYDROGENATION CATALYST

[75] Inventor: Jan F. Van Peppen, Chester, Va.

[73] Assignee: Allied Corporation, Morris Township, Morris County, N.J.

[21] Appl. No.: 364,109

[22] Filed: Mar. 31, 1982

[51] Int. Cl.$^3$ .................... B01J 23/96; B01J 23/38; C07C 45/00; C07C 29/20
[52] U.S. Cl. ............................. 502/25; 260/690; 564/423; 568/362; 568/835; 502/29
[58] Field of Search ................. 252/411 R, 412, 413, 252/414, 447; 568/362

[56] References Cited

U.S. PATENT DOCUMENTS

| | | |
|---|---|---|
| 967,919 | 8/1864 | Viscosa. |
| 2,829,166 | 4/1958 | Joris et al. .......................... 568/362 |
| 2,857,337 | 10/1958 | Hamilton et al. ................... 252/472 |
| 2,862,890 | 12/1958 | Daughery, Jr. et al. ............ 252/412 |
| 2,901,419 | 8/1959 | Brill ................................ 252/411 R |
| 3,076,810 | 2/1963 | Duggan et al. ..................... 568/362 |
| 3,305,586 | 2/1967 | Phielix ............................... 568/362 |
| 3,356,729 | 12/1967 | Denton et al. ..................... 564/423 |
| 3,457,187 | 7/1969 | Armstrong et al. ................ 252/430 |
| 4,088,568 | 5/1978 | Schwartz ........................... 252/417 |
| 4,122,040 | 10/1978 | McCarroll et al. ................ 252/447 |
| 4,145,314 | 3/1979 | Fung et al. ......................... 252/437 |
| 4,147,660 | 4/1979 | Yamauchi et al. ................. 252/412 |
| 4,152,291 | 5/1979 | Drake ................................ 252/416 |
| 4,171,288 | 10/1979 | Keith et al. ........................ 252/462 |
| 4,203,923 | 5/1980 | Yeh et al. .......................... 568/362 |
| 4,242,235 | 12/1980 | Cognion et al. ................. 252/455 R |

FOREIGN PATENT DOCUMENTS

| | | | |
|---|---|---|---|
| 741994 | 5/1970 | Belgium ........................ 252/411 R |
| 2722771 | 12/1977 | Fed. Rep. of Germany ...... 252/447 |

*Primary Examiner*—P. E. Konopka
*Attorney, Agent, or Firm*—Richard A. Anderson

[57] ABSTRACT

This invention is a method to restore the metal content of a supported noble metal hydrogenation catalyst comprising adding the appropriate amount of a noble metal salt of a weak acid to a fluid feed passing across the catalyst.

7 Claims, No Drawings

METHOD TO RESTORE THE METAL CONTENT OF A NOBLE METAL HYDROGENATION CATALYST

BACKGROUND OF THE INVENTION

This invention relates to a method to restore the metal content of a supported noble metal hydrogenation catalyst comprising adding the appropriate amount of a noble metal salt of a weak acid to a fluid feed passing across the catalyst. For example, palladium content of the catalyst used for hydrogenation of phenol can be restored by adding the appropriate amount of a weak acid salt of palladium, such as palladium phenate, in the phenol before it passes over the catalyst.

Noble metal catalysts, such as palladium, are well known in the prior art for various reactions. See U.S. Pat. Nos. 2,829,166; 2,857,337; 3,076,810; 3,305,586; 3,457,187; 3,356,729; 4,203,923 and 4,152,291, all of which are hereby incorporated by reference. Also, British Pat. No. 967,919 discloses hydrogenating benzoic acid to hexahydrobenzoic acid. Other noble metal catalyzed processes are disclosed in U.S. Pat. Nos. 4,242,235 (silver); 4,171,288 (platinum group); 4,147,660 (platinum group); 4,145,314 (Group VIII metal group) and 4,122,040 (platinum group), also incorporated by reference.

Previously, as explained at the bottom of column 1 to column 2 of U.S. Pat. No. 3,305,586, it was necessary to rejuvenate catalyst by adding fresh, virgin catalyst to the reaction mass, or to counteract poisons with promoters as disclosed in U.S. Pat. No. 3,076,810. Promoters are also included in this invention and would supplement it. For example, a hydrogenation of phenol to cyclohexanone involves a palladium catalyzed reaction between phenol and hydrogen. Production capacity and also the amount of undesirable by-product formation depend primarily on the quality of the palladium catalyst which is present in the continuous process loop. Feedstock contaminants capable of irreversible adsorption on the catalyst deactivate the catalyst. Loss of palladium from the surface of the catalyst renders the catalyst less effective. Presently, the quality of the catalyst is maintained through a catalyst purge and make-up procedure. This method has several disadvantages. Other rejuvenation procedures also are impractical.

The catalyst, 5% (as charged) palladium on carbon, in the phenol hydrogenation process loses activity and selectivity. This deterioration is a result of palladium disappearance from the catalyst, strongly adsorbed extraneous compounds and thermal rearrangement of the palladium on the surface of the catalyst. Rejuvenation procedures developed in the past involved a cleansing of the catalyst surface through extraction with liquids. The effectiveness of these procedures depends on the nature of the adsorbate; the palladium content and palladium dispersion are not restored. Furthermore, these rejuvenation procedures are cumbersome and impractical since they involve the removal of the catalyst from the process loop, an extraction process and return to the loop. Poor catalyst performance, as a result of acute or chronic catalyst poisoning, is usually remedied by higher than normal purging of catalyst and replacement with virgin catalyst. The latter is undesirable because it lowers the total amount of solids in the loop, which causes instability in the process operation. Furthermore, excessive catalyst purging is expensive due to high palladium conversion costs. A method which can restore the activity and the selectivity of the catalyst present in the process loop without the disadvantages mentioned above would be desirable and essential for capacity increase.

Other catalysts used in industrial processes also invariably experience deactivation. The deactivation can be caused by contaminants in the feedstock through formation of inhibitors on the surface of the catalyst, by thermal rearrangement of the active sites on the catalyst or by disappearance of metal from the support in the case of a supported catalyst.

In the phenol hydrogenation process, catalyzed by supported palladium, the catalyst also becomes deactivated in varying degrees. Thus, it has been observed that the catalyst present in the continuous process loop has only one-tenth the activity of the virgin make-up catalyst. The degree of deactivation can often times be correlated with impurities in the phenol feedstock. For instance, low oxidation state sulfur compounds when present in phenol are a prime cause for deactivation. Acetol, a known by-product in the cumene phenol process decomposes to carbon monoxide on the surface of the catalyst and thus deactivates the catalyst. Small amounts of iron and nickel entering the process with phenol and with hydrogen gas cause catalyst deactivation. Iron and nickel furthermore catalyze the undesirable conversion of phenol directly to cyclohexanol to a much greater extent than palladium does. Iron and nickel, therefore, lower the selectivity of the catalyst. Other agents such as organic and inorganic acids and amines are known to lower the activity and the selectivity of the catalyst.

The underlying reason for deactivation is simply the fact that one ingredient or another in the process is adsorbed on the active sites of the catalyst much more strongly than phenol. In the case of selectivity loss, the reason can be twofold: (1) the specific active sites adsorbing phenol are blocked more than different active sites adsorbing cyclohexanone or (2) other metals, such as iron or nickel, adsorbed on the catalyst convert phenol to cyclohexanol. When the expressions "ol" and "one" are used herein, they mean cyclohexanol and cyclohexanone, respectively.

The disappearance of palladium from the catalyst also leads to lower activity. The disappearance of palladium from the carbon support in the hydrogenation process is an established fact. While the catalyst supplied to the process contains 5% palladium, this level readily drops in the process to a lower level. The mechanism of disappearance is understood only in part. It is known that the small particle size fraction of the catalyst, containing a disproportionally high palladium content, is not retained in the continuous process loop by the centrifuges. Escape of the small particle size portion, therefore, results in a loss of palladium; but this does not adequately account for all of the palladium lost. It is speculated that two other mechanisms are involved. One of these is related to the observed presence of palladium salt, rather than palladium metal only, on the virgin catalyst. Presumably the palladium salt became dissolved into the process liquids and thus became lost from the catalyst. The other possible mechanism involves the dissolution of palladium as a palladium hydride encouraged by metal complexing agents such as amines present in the process liquids. Evidence for the latter is the fact that palladium has been found to plate out in the areas of the process having low or zero hydrogen pressure. A dissolved palladium hydride molecule forced to give up its hydrogen and not capable of reconstituting it will precipitate from the solution.

In summary, deactivation and loss of selectivity appear to be a result of loss of active sites through (1) a very tenacious masking process and (2) escape. On the basis of these conclusions, we have devised a procedure to restore the characteristics of favorable activity and selectivity in a used catalyst to any degree desirable.

By weak acid herein is meant any anion conjugated with an acid having a dissociation constant, pKa, greater than 3.00.

SUMMARY OF THE INVENTION

This invention is a method to restore the metal content of a supported noble metal catalyst comprising adding the appropriate amount of noble metal salt of a weak acid to the fluid feed passing across the catalyst. The preferred noble metals are selected from a group consisting of silver, platinum, palladium, irridium, rhodium, ruthenium, osmium and mixtures thereof. The anion of the weak acid salt of the noble metal is selected from the group consisting of acetylacetonate, phenate, formate, acetate, propionate, butyrate, stearate, benzoate, oxalate, malonate, succinate, glutamate, adipate and mixtures thereof. The preferred noble metal catalyst is palladium. The preferred anion of the weak acid salt is phenate. The preferred fluid feed contains an unsaturated aromatic moiety. The fluid feed can be selected from the group consisting of hydrogen, phenol, aromatic nitro compounds, benzoic acid, olefinically unsaturated compounds, nitrocycloalkylanes, nitroalkylanes, petroleum hydrocarbons, and mixtures thereof. The support for the noble metal catalyst can be selected from a group consisting of carbon, kieselguhr, silica, alumina, calcium carbonate, asbestos, pumice, clays and mixtures thereof. The preferred support is finely divided carbon. The most preferred feed is a mixture of phenol and hydrogen. When using the most preferred feed of phenol and hydrogen, the catalyst is present in an amount from about 0.2 to about 5 percent palladium on a finely divided carbon support and the noble metal salt used to restore the catalyst is the palladium salt of a weak acid, preferably a phenate. It could also be an acetate or an acetylacetonate. Even more preferred when hydrogenating phenol, the catalyst would be present in an amount between about 0.1 and 15 percent by weight of the reaction mass, phenol is present in an amount between about 1 and 99 percent by weight of the reaction mass, and hydrogen is present in an amount between 0.01 and 5 percent of the reaction mass. The hydrogenation of phenol takes place at a temperature of about 120° and 200° C. and a pressure of between about 10 ($6.8^9 \times 10^4$ pascals) and 500 ($3.4 \times 10^6$ pascals) psig and a flow rate of between about 1000 (28 cubic meters) and 20,000 (560 cubic meters) cubic feet of hydrogen per minute and between about 10 (38 liters) and 150 (570 liters) gallons per minute of phenol. It is preferred to add the palladium salt to the phenol feed in an amount between about 0.01 (4.5 grams) and 20 (9000 grams) pounds per hour.

DESCRIPTION OF THE PREFERRED EMBODIMENT

A catalyst having its active sites masked or otherwise lost in the extreme is not unlike the carbon support without palladium. Carbon support without palladium is, of course, the material used by the catalyst manufacturer to produce the catalyst. In the catalyst manufacture, the carbon support is impregnated with palladium salt which is subsequently reduced to palladium metal. Similarly, in the present catalyst reconditioning procedure, palladium salt was added to a used catalyst to restore the active sites content. There is, however, a fundamental deviation from the catalyst manufacture procedure.

We have observed in the past, and again recently, that palladium chloride cannot be reduced readily to palladium metal under the phenol hydrogenation reaction conditions. Palladium acetate, palladium acetylacetonate, and palladium phenate on the other hand were reduced fully to palladium metal under the hydrogenation reaction conditions. It appears from these findings that the ease of reduction of the palladium in the oxidation state of two was a function of the nature of the anion of the salt. The stronger the corresponding acid of the anion the less its willingness to be reduced. The above mentioned palladium salt reductions were carried out in the presence of a palladium on carbon catalyst. In the absence of palladium on carbon, none of the palladium salts were reduced to a meaningful extent.

The present procedure, therefore, is characterized in that the palladium salt used was the salt of a very weak acid, such as an acetate, acetylacetonate or a phenate salt. Also characteristic of the procedure is that the palladium salt of choice was added to the process in situ. In a typical experiment, therefore, phenol, used catalyst, the palladium salt and an amount of sodium hydroxide stoichiometic to the palladium salt were charged to the reactor. At a temperature of 160° C., hydrogen was supplied and the reaction proceeded. Reduction of the palladium salt by hydrogen took place prior to or simultaneous with phenol reduction, whereupon the reduced palladium became an integral part of the used catalyst present. The improvement of catalyst performance can best be assessed by the data of Table 1. In all of the experiments, the amount of palladium salt added represented a 1 percent increment of palladium on the catalyst. Experiment No. 494 shows that the phenol conversion was extremely slow when palladium acetylacetonate only was used as catalyst. However, in conjunction with recycle catalyst B, sampled from a reactor and washed with hexane, palladium acetylacetonate was a very active promoter as shown in the duplicate experiments No. 496 and No. 498 and compared with the experiments No. 495 and No. 497 having the palladium salt left out. The latter two experiments differ in the amounts of caustic added. It is known that base is a catalyst promoter in the phenol hydrogenation. The aspect of caustic requirement in these experiments is ambiguous. We have assumed that when a palladium salt is reduced the anion of the salt will form its corresponding acid.

Therefore, in the experiments with palladium salts, 2 moles of sodium hydroxide were added per mole of palladium salt. This reasoning may not be entirely correct since, for instance, the sodium salt of acetylacetonate when formed will still be a considerably strong base and as such will be of some benefit to the hydrogenation rate, similar to the rate enhancement experienced with sodium carbonate or sodium phenate. On the other hand, sodium chloride, formed when palladium chloride is used, will not be beneficial to the catalyst. Thus, experiment No. 497, having the same amount of caustic as in the experiments containing the palladium acetylacetonate, Nos. 496 and 498, had a rate of only one-half of that with the palladium salt, while experiment No. 495, having no sodium hydroxide added, was only one-third as fast as the palladium salt-containing experiments. With respect to the selectivity (k"one"/k"ol"), the palladium salt addition showed an enormous improvement over the control experiments, with and without sodium hydroxide added. The amount of cyclohexanol formed in the batch reaction is, of course, subject to the total reaction time. This makes it difficult to assess the selectivity of a catalyst on the basis of percent cyclohexanol formed at 95 percent phenol conversion, particularly when the total reaction times vary significantly. For these reasons, an experiment was devised which had a reaction time more corresponding to the control experiments Nos. 495 and 497. In this experiment, No. 499, only one-half of the amount of recycle catalyst and one-half of the amount of palladium salt of experiments Nos. 496 and 498 were used. Still, the total amount of cyclohexanol formed over a longer reaction time was less with the palladium salt than in the control experiments.

In Table 2 is shown the effect of the anion of the palladium salt. Clearly, the activity and the selectivity decreased when going from acetylacetonate to acetate and to chloride. The rates paralleled the strength of the acid corresponding with the anion, the stronger the acid the lower the activity and the selectivity. Another consideration here is the previously established rate inhibiting effect of chloride which may have affected the rate in the experiment No. 500.

To investigate further the improvements in activity and selectivity of various recycle catalysts through palladium salt addition, the experiments in Table 3 were carried out. The A recycle catalysts used in these experiments date back to the time when the "one"/"ol" ratio in the commercial process was consistently low. Treatment with hot water and hot caustic improved this recycle catalyst to some extent, but not to an acceptable level. In experiments Nos. 418 and 502, the effect of palladium acetylacetonate on identical recycle catalyst is shown. Although only one-half of the usual catalyst charge was used in experiment No. 502, having the palladium salt added, the rate of phenol conversion was essentially the same while the selectivity improved considerably. More pronounced differences in activity and selectivity would have been found with more than the stoichiometrically required amount of sodium hydroxide, as elaborated above, In the experiments Nos. 419, 503 and 504, the effect of palladium salt on an inferior caustic washed catalyst was determined. As in the previous experiments, added palladium salt to one-half of the standard catalyst charge had the same rate obtained with the standard catalyst charge. In the experiment No. 504, the amount of sodium hydroxide added was increased to satisfy the palladium salt stoichiometry and an amount equivalent to that in experiment No. 419 (without palladium salt added). The activity in this experiment improved further, as did the selectivity. In the experiments Nos., 495 and 499, the effect of palladium salt is shown on a more recent recycle catalyst. Again, one-half the standard catalyst charge with palladium salt showed a higher rate than that obtained with the standard charge. The selectivity had improved substantially.

Added to recycle catalyst, palladium phenate, dissolved in phenol, was found to outperform palladium acetate. The palladium phenate solution was prepared by removing acetic acid from a palladium acetate solution in phenol through distillation; see Table 4. The rate enhancement effect of palladium acetate on recycle catalyst was extended to carbon black. Palladium phenate solution in phenol and carbon black added separately to the reactor generated a catalyst which had good activity, and high selectivity with the carbon black normally used to prepare standard catalyst. A different type carbon black from another source was much less effective. The results are shown in Table 5. The catalyst thus generated was similar in performance to a 1 percent Pd/C catalyst prepared commercially. When the palladium phenate and the carbon black were combined outside of the reactor (as opposed to in situ), the activity was the same as that obtained with the in situ generated catalyst but the selectivity was not as good.

Multiple phenol hydrogenation cycles were carried out with recycle catalyst promoted with 1 percent palladium as palladium acetate in the first cycle only. The results are shown in Table 6. The catalyst retained its high activity and selectivity over 12 cycles.

The disposition of the added palladium was determined by atomic adsorption and Electron Spectroscopy for Chemical Analysis (ESCA). The results are shown in Table 7. All of the palladium added as acetylacetonate was found on the catalyst recovered from the hydrogenation experiment and nearly so with the acetate as determined by atomic adsorption. When added as the chloride, the recovered catalyst contained considerably less than the amount added. More revealing are results obtained by ESCA which provide a measure of the palladium content on the surface only (probing depth of approximately 15 angstrom). The catalysts resulting from 1 percent palladium acetate and palladium acetylacetonate addition showed a 23-fold increase in surface palladium. These data can be interpreted as a surface palladium content of 13 to 14 percent on catalysts containing approximately 2.4 percent palladium. This kind of surface palladium level exceeds that of virgin catalyst by a factor of 2–3.

Palladium chloride was found much less effective in the surface palladium enrichment. Also, the palladium on the catalyst reconditioned with a weak acid salt of palladium was of the metallic form. The reduction of the $Pd^{2+}$ to $Pd°$ under the phenol hydrogenation conditions appear to be very facile for weak acid salts.

HYDROGENATION OF BENZOIC ACID

An autoclave having 3 liter capacity is employed, of Inox stainless steel, with electromagnetic stirring (120 stirring strokes in 1 minute), providing internally with a candle filter (size of candle filter external diameter 24 mm, height 120 mm), for hydrogenation; and an autoclave of 1 liter capacity of Inox stainless steel for the charging of the mixture of benzoic acid and hexahydrobenzoic acid, as will be said afterwards.

Seven hundred grams of hexahydrobenzoic acid, 300 grams of benzoic acid produced by oxidation of toluene and purified by means of crystallization from water and 20 grams of palladium catalyst with 5 percent of metal on charcoal, equivalent to 0.333 percent of metal on benzoic acid, are charged into the 3-liter capacity autoclave. The latter is washed with $N_2$, is charged with $H_2$ at 130 atmospheric pressure and is heated to a temperature of 130° C. The hydrogenation is carried out at 130°–135° C. in a pressure interval of from 150 to 100 atmospheres (10.3 to 6.89×10⁵ pascals) and in about 1 hour's time. At the end of hydrogenation, the autoclave is cooled down to 90° and its content is filtered through the candle placed inside the autoclave. Eight hundred grams of hexahydrobenzoic acid (100 percent according to the index of refraction) are discharged while 200 grams thereof remain in the autoclave.

The discharge is divided into 2 parts; 300 grams go to production and 500 grams to which 300 grams of fresh benzoic acid and 0.42 gram of palladium acetate is added, are charged into the hydrogenation autoclave by means of a slight nitrogen pressure (about 2 atmospheres) (1.3×10⁴ pascals) through a candle filter, in a direction reversed with respect to discharge, so as to permit the return into suspension of the catalyst cake remained adherent on the walls of the candle. Then the autoclave is washed with nitrogen, the H₂ is charged at 130 atmospheres (8.9×10⁵ pascals) and the temperature is brought up to 130° and the mixture is hydrogenated. The cycles can be repeated indefinitely by charging a fresh mixture of benzoic acid, palladium acetate and hexahydrobenzoic acid according to the technique indicated previously.

METHOD TO RESTORE METAL CONTENT IN A VAPOR PHASE PROCESS

Example 1 of U.S. Pat. No. 3,305,586 is hereby incorporated by reference, in toto.

After several months of operation, the hourly weight production yield begins to diminish and the amount of cyclohexanol formed begins to increase. The continuous process is interrupted. The solid catalyst bed is flooded with a solution of 10.6 kilograms of palladium acetate in 2000 kilograms of phenol. After 2 hours, the liquids are drained from the bed and the continuous operation as described above is resumed. The hourly weight production yield is improved and the amount of cyclohexanol formed per hour is less.

The following example which illustrates a preferred embodiment of this invention is presented without any intention of being limited thereby. All parts and percentages are by weight unless otherwise specified.

EXAMPLE 1

An alcohol solution of dinitrotoluene was prepared by agitating molten technical grade dinitrotoluene (approximately 80 percent 2,4- and 20 percent 2,6-dinitrotoluene) and 0.75 percent of palladium acetate in methanol at a temperature of about 50° C. Three pounds (1361 grams) of methanol were employed for each pound (454 grams) of molten dinitrotoluene.

The reactor employed for the reaction was a five-gallon (19 liter) autoclave provided with internal and external coils to adjust the reaction temperature as desired. The reactor was also provided with a mechanical agitator having a speed of 600 revolutions per minute. Secured to the agitator shaft was a four-inch (10.16 cm) diameter turbine-type agitator and a four-inch (10.15 cm) diameter propeller-type agitator, the turbine being positioned about one-third of a reactor diameter up from the reactor bottom and the propeller being positioned about one reactor diameter up from the reactor bottom along the shaft. Feed lines for the dinitrotoluene and hydrogen were secured to dip tubes positioned within the autoclave to discharge directly into the eye of the four-inch (10.16 cm) turbine to ensure immediate mixing of both the dinitrotoluene and the hydrogen with the reactor contents. Six porous stainless steel filter elements were secured within the autoclave to permit separation of the product effluent from the catalyst particles. The catalyst used was a commercial 5 percent palladium on carbon catalyst.

One pound (454 grams) of 5 percent palladium on carbon catalyst was mixed in three gallons (11.36 liters) of methanol and the slurry charged to the reactor which was then pressurized to 400 psig (27.55×10⁵ pascals) with hydrogen, agitated, and heated to a temperature of 105° C. These temperature, pressure, and agitator conditions were maintained throughout the reaction. The alcohol solution of dinitrotoluene was then fed to the reactor through a steam traced line to maintain the solution at about 50° C. in the line. The rate of feed of the alcohol solution of dinitrotoluene was about 22.7 pounds (10 296 grams) per hour, which was equivalent to a catalyst loading of 0.062 pound-equivalent of nitro groups per hour per pound of catalyst (0.062 gram-equivalent of nitro groups per hour per gram of catalyst), and the simultaneous feed rate of hydrogen was at the rate of about 0.37 pound (168 g) per hour. The feed of palladium acetate was 0.21 pound (95 grams) per hour. Product was withdrawn from the autoclave at the rate of about 23.1 pounds (10 487 grams) per hour. Equilibrium was quickly attained, and the average analysis of the product obtained during the reaction was 16.5 percent toluene diamine, 0.5 percent residue, 0.004 percent reducibles, 73.2 percent methanol, and 9.8 percent water. The reaction was continued indefinitely.

BENEFITS OF THE INVENTION

Virgin catalyst when added in the process loses its good qualities rapidly as a result of loss of small pores and to some extent due to masking of some of its palladium by poisons. Thus, the transition of virgin catalyst to recycle catalyst does not take long in the process. Superiority of the virgin catalyst lies in a given number of active sites advantageously distributed over a large surface area which includes small pores. We have demonstrated in the past that most of the overall surface area is found in the small pores, and that they become plugged up rapidly in the process. The active sites located in the small pores are then no longer available for catalytic action.

The reconstituted recycle catalyst of this invention draws its improved activity from a great multitude of active palladium sites chemisorbed on a surface no longer subject to loss of small pores. Because of the usual difference in the relative concentrations of virgin and recycle catalyst in a reaction having similar rates, the aggregate surface area of the catalyst (virgin or recycle) will be comparable in size though entirely different in nature as explained in the foregoing. Deposition of palladium on the aggregate surface area of recycle catalyst has, therefore, the advantages of more favorable dispersion and longer lasting quality (loss of pores will be minimal).

In summary, the superior qualities of virgin catalyst will become irretrievably lost in recycling due to the small pores loss mechanism as opposed to the long lasting qualities of palladium deposited on an aged surface area. The reconstitution of recycle catalyst by means of this invention is not proposed to merely substitute virgin catalyst addition, but it aims to rather permanently improve the quality of all of the catalyst in residence in a commercial process.

With respect to the selectivity considerations only, the selectivity obtained with virgin catalyst is shortlived as evidenced by the following. When the formation of "ol" in a hydrogenation reaction is evaluated over the 20-50% conversion period versus the 50-80% conversion period, it is found to be much higher in the early stages of the reaction. This is rationalized by the change in dielectric constant of the medium (phenol changing to "one") and also the consequent increasing sodium content on the catalyst. With a virgin catalyst, however, the formation of "ol" in the first part of the reaction is much the same as that in the second part. Hence, selectivity became less as the reaction proceeded. Reconstitution of catalyst by means of this invention, on the other hand, intensifies the difference in "ol" formation between the early and later conversion periods which is evidence for permanency of selectivity. Also, the selectivity obtained with virgin catalyst is less than that found with a promoted recycle catalyst of this invention having the same activity.

TABLE 1
HYDROGENATION PERFORMANCE IMPROVEMENT THROUGH PALLADIUM SALT ADDITION

| Experiment (1) | Recycle Catalyst, Grams(2) | | Pd Acetylacetonate(3) | | NaOH(4) | |
|---|---|---|---|---|---|---|
| | | | mg | m Mole | ml | m Mole |
| 494 | None | — | 129 | 0.40 | 0.30 | 0.75 |
| 496/498 | 9 | B | 260 | 0.86 | 0.68 | 1.7 |
| 495 | 9 | B | — | — | — | — |
| 497 | 9 | B | — | — | 0.68 | 1.7 |
| 499 | 4.5 | B | 130 | 0.43 | 0.34 | 0.85 |

| Experiment (1) | k"one" × $10^{-3}$ Min$^{-1}$ | k"ol" × $10^{-3}$ Min$^{-1}$ | k"one"/k"ol" |
|---|---|---|---|
| 494 | 8 Percent conversion in 4 hours | | |
| 496/498 | 34.1 | 0.29 | 119 |
| 495 | 11.1 | 0.23 | 49 |
| 497 | 17.0 | 0.22 | 78 |
| 499 | 15.6 | 0.15 | 103 |

| Experiment (1) | Time to 95% Conversion, Minutes | % "ol" at 95% Conversion |
|---|---|---|
| 494 | 8 Percent conversion in 4 hours | |
| 496/498 | 71 | 1.0 |
| 495 | 270 | 3.2 |
| 497 | 140 | 1.5 |
| 499 | 165 | 1.4 |

(1)900 Grams phenol (purified), 160° C., 80 psi (5.51 × 10$^5$ pascals) hydrogen.
(2)Recycle catalyst was obtained from a commercial reactor slurry sample, washed with hexane and dried.
(3)The amount of palladium added represents 1% based on catalyst.
(4)Ten percent aqueous solution.

TABLE 2
EFFECT OF THE ANION OF THE PALLADIUM SALT

| Experiment (1) | Palladium Salt(2) | | | NaOH(3) | |
|---|---|---|---|---|---|
| | Type | mg | m Mole | ml | m Mole |
| 499 | Acetylacetonate | 130 | 0.43 | 0.34 | 0.85 |
| 501 | Acetate | 95 | 0.42 | 0.34 | 0.85 |
| 500 | Chloride | 75 | 0.42 | 0.34 | 0.85 |

| Experiment (1) | k"one" × $10^{-3}$ Min$^{-1}$ | k"ol" × $10^{-1}$ Min$^{-1}$ | k"one"/k"ol" |
|---|---|---|---|
| 499 | 15.6 | 0.15 | 103 |
| 501 | 13.9 | 0.19 | 73 |
| 500 | 8.7 | 0.15 | 58 |

| Experiment (1) | Time to 95% Conversion, Minutes | % "ol" at 95% Conversion |
|---|---|---|
| 499 | 165 | 1.4 |
| 501 | 173 | 1.6 |
| 500 | 285 | 2.5 |

(1)900 Grams phenol (purified), 4.5 grams recycle catalyst C (hexane washed and dried), 160° C., 80 psi (5.51 × 10$^5$ pascals) hydrogen.
(2)The amount of palladium added represents 1% based on catalyst.
(3)Ten percent aqueous solution.

TABLE 3
EFFECT OF PALLADIUM SALT ON VARIOUS RECYCLE CATALYST

| Experiment (1) | Recycle Catalyst Amount, Grams | | Palladium(5) Acetylacetonate | | NaOH(6) | |
|---|---|---|---|---|---|---|
| | | | mg | m Mole | ml | m Mole |
| 418(2) | A | 9 | — | — | 0.63 | 1.58 |
| 502(2) | A | 4.5 | 130 | 0.43 | 0.34 | 0.85 |
| 419(3) | A | 9 | — | — | 0.63 | 1.58 |
| 503(3) | A | 4.5 | 130 | 0.43 | 0.34 | 0.85 |
| 504(3) | A | 4.5 | 130 | 0.43 | 0.66 | 1.64 |
| 495(4) | B | 9 | — | — | — | — |
| 499(4) | B | 4.5 | 130 | 0.43 | 0.34 | 0.85 |

| Experiment (1) | k"one" × $10^{-3}$ Min$^{-1}$ | k"ol" × $10^{-3}$ Min$^{-1}$ | k"one"/k"ol" |
|---|---|---|---|
| 418(2) | 6.5 | 0.21 | 31 |
| 502(2) | 6.4 | 0.13 | 48 |
| 419(3) | 12.6 | 0.27 | 47 |
| 503(3) | 9.4 | 0.18 | 54 |
| 504(3) | 11.9 | 0.14 | 87 |
| 495(4) | 11.1 | 0.23 | 49 |
| 499(4) | 15.6 | 0.15 | 103 |

(1)900 Grams phenol (purified), 160° C., 80 psi (5.51 × 10$^5$ pascals) hydrogen.
(2)Recycle catalyst was obtained from a commercial slurry washed with hexane and six times with water at 100° C., then dried.
(3)Recycle catalyst was obtained from a commercial reactor slurry, washed with hexane, twice with 10% caustic at 100° C., and four times with hot water, then dried.
(4)Recycle catalyst was obtained from a commercial reactor slurry, washed with hexane and dried.
(5)The amount of palladium added represents 1% based on catalyst.
(6)Ten percent aqueous solution.

TABLE 4
EFFECT OF ACETIC ACID REMOVAL ON CATALYST PERFORMANCE(1)

| Experiment | Palladium Salt | k"one" × $10^{-3}$ Min$^{-1}$ | k"ol" × $10^{-3}$ Min$^{-1}$ | k"one"/k"ol" | 95% Conversion Time, Minutes | "ol", % |
|---|---|---|---|---|---|---|
| 505 | Pd acetate dissolved in phenol(2) | 16.2 | 0.16 | 103 | 153 | 1.1 |
| 506 | Pd phenate dissolved | 18.1 | 0.14 | 131 | 134 | 1.0 |

TABLE 4-continued
EFFECT OF ACETIC ACID REMOVAL ON CATALYST PERFORMANCE[1]

| Experiment | Palladium Salt | k"one" × 10⁻³ Min⁻¹ | k"ol" × 10⁻³ Min⁻¹ | k"one"/ k"ol" | 95% Conversion Time, Minutes | "ol", % |
|---|---|---|---|---|---|---|
| | in phenol[3] | | | | | |

[1]Hydrogenation experiment:
900 Grams phenol
4.5 Grams recycle catalyst B
Equivalent of 1% Pd added as Pd salt
65.5 Mg NaOH (sum of 4000 ppm Na+ on catalyst and stoichiometric requirement for Pd salt), 160°C., 80 psi (5.51 × 10⁵ pascals) hydrogen.
[2]Pd acetate was added as a solution of 0.095 gram Pd acetate (0.045 gram palladium) in 20 grams phenol.
[3]Pd phenate solution was prepared as follows:
A solution of 0.475 gram of Pd acetate in 99.5 grams phenol was subjected to distillation under vacuum; approximately one-half of the phenol was distilled over. The weight of the residue was restored to 100 grams. Of this solution, 20 grams containing 0.045 gram palladium as palladium phenate was used.

TABLE 5
PERFORMANCE OF CATALYST PREPARED FROM PALLADIUM SALT AND CARBON BLACK[1]

| Experiment | Catalyst | k"one" × 10⁻³ Min⁻¹ | k"ol" × 10⁻³ Min⁻¹ | k"one"/ k"ol" | 95% Conversion Time, Min. | "ol", % |
|---|---|---|---|---|---|---|
| 507 | Pd phenate (equivalent to 1% Pd) + carbon black normally used to prepare standard catalyst[2] | 11.5 | 0.12 | 99 | 216 | 2.3 |
| 510 | Pd phenate[2] (equiv. to 1% Pd) + carbon black; alternate source | 8.0 | 0.28 | 28 | >300 | >5 |
| 511 | Pd on carbon prepared from Pd phenate[2] and carbon black[3] | 11.5 | 0.17 | 69 | 223 | 3.1 |

[1]See Table 4, footnote[1]. Catalyst recovered from Experiment 507 contained 0.79% Pd (not corrected by TGA loss)
[2]See Table 4, footnote[2]
[3]Whereas in Experiments 507 and 510 the catalyst was generated in situ; in the experiment 511, palladium phenate was deposited on carbon black (normally used to prepare standard catalyst) from a phenol solution then filtered and dried (0.82% Pd by analysis); subsequently 4.5 grams was used as catalyst.

TABLE 6
MULTIPLE CYCLES WITH ONCE PALLADIUM ACETATE PROMOTED RECYCLE CATALYST[a]

| Cycle | Expt. | Caustic Sodium, ppm | k"one" × 10⁻³ Min⁻¹ | k"ol" × 10⁻³ Min⁻¹ | k"one"/k"ol" | Time, Min. | 95% Conversion "ol", % | "one"/"ol" |
|---|---|---|---|---|---|---|---|---|
| 1 | — | — | — | — | — | — | — | — |
| 2 | 512 | 4000 | 22.7 | 0.30 | 76 | 90–100 | 1.70 | 55 |
| 3 | 513 | 4000 | 26.3 | 0.25 | 104 | 88 | 1.28 | 78 |
| 4 | 514 | 4000 | 42.2 | 0.34 | 123 | 76 | 1.30 | 72 |
| 5 | 515 | 4000 | 31.7 | 0.22 | 144 | 76 | 1.20 | 78 |
| 6 | 516 | 4000 | 34.8 | 0.26 | 133 | 68 | 1.17 | 80 |
| 7 | 517 | 2000 | 29.6 | 0.26 | 115 | 77 | 1.22 | 77 |
| 8 | 518 | 2000 | 27.8 | 0.25 | 113 | 82 | 1.23 | 76 |
| 9 | 519 | 4000 | 31.7 | 0.22 | 143 | 73 | 1.13 | 83 |
| 10 | 520 | 2000 | 27.0 | 0.23 | 119 | 70 | 1.10 | 85 |
| 11 | 521 | 2000 | 30.0 | 0.25 | 118 | 79 | 1.22 | 77 |
| 12 | 522 | 2000 | 25.5 | 0.26 | 99 | 83 | 1.35 | 69 |

[a]900 Grams phenol. 9 Grams catalyst, promoted in the first cycle with 0.190 gram palladium acetate. NaOH was added as a 10% aqueous solution. 160° C., 80 psi (5.4 atmospheres) (3.72 × 10⁴ pascals) hydrogen.

TABLE 7
DETERMINATION OF PALLADIUM ON RECONDITIONED CATALYSTS[a]

| Expt. | Palladium Salt | Palladium % On Catalyst | Palladium on Surface [b]Pd:C (ESCA) | Bulk Pd Content (Atomic Adsorption), % |
|---|---|---|---|---|
| 497 | None | 0 | 0.006 | 1.47 |
| 496 | Acetyl acetonate | 1 | 0.131 | 2.42 |
| 501 | Acetate | 1 | 0.140 | 2.29 |
| 500 | Chloride | 1 | 0.016 | 1.89 |
| — | Virgin catalyst (Englehard) | 5 | 0.055 [b] | 5.0 |

[a]The catalyst was recovered from the hydrogenation reaction mixture, washed with hexane, and dried.
[b]By ESCA (Electron Spectroscopy for Chemical Analysis).

I claim:
1. A method to restore metal content of a supported noble metal catalyst in a reaction mass comprising adding the appropriate amount of a salt of a weak acid of said noble metal to a fluid feed passing across the catalyst wherein the feed is phenol and hydrogen.

2. The method of claim 1 wherein the catalyst is from about 0.2 to about 5 percent by weight palladium on finely divided carbon support.

3. The method of claim 2 wherein the catalyst is present in an amount between about 0.1 and 15 percent by weight of the reaction mass, phenol is present in an amount between about 1 and 99 percent by weight of the reaction mass, hydrogen is present in an amount between about 0.01 and 5 percent by weight of the reaction mass, the hydrogenation of phenol takes place at a temperature between about 120° and 200° C., a pressure between about 10 ($6.89 \times 10^4$ pascals) and 500 ($3.4 \times 10^6$ pascals) psig and a flow rate of between about 1000 (28 m$^3$) and 20 000 (560 m$^3$) cubic feed of hydrogen per minute and between about 10 (38 liters) and 150 (570 liters) gallons per minute of phenol.

4. The method of claim 3 wherein the palladium salt is added to the phenol feed in an amount between about 0.01 (4.5 grams) and 20 (9000 grams) pounds per hour.

5. The method of claim 4 wherein the palladium salt is the phenate.

6. The method of claim 4 wherein the palladium salt is the acetate.

7. The method of claim 14 wherein the palladium salt is the acetylacetonate.

* * * * *